United States Patent [19]

Walker

[11] Patent Number: 5,098,414
[45] Date of Patent: Mar. 24, 1992

[54] STEAMING DEVICE FOR COSMETIC SKIN TREATMENT

[76] Inventor: Cedric T. M. Walker, 1900 South Eads St., Apt. 933, Arlington, Va. 22202

[21] Appl. No.: 466,597

[22] Filed: Jan. 17, 1990

[51] Int. Cl.⁵ .............................................. A61F 7/00
[52] U.S. Cl. .................................... 604/291; 604/315; 128/368; 4/537
[58] Field of Search ................................ 604/23-24, 604/289-291, 303, 315; 128/367-368, 375; 4/537; 34/96, 97

[56] References Cited

U.S. PATENT DOCUMENTS

| | | | |
|---|---|---|---|
| 1,421,756 | 7/1922 | Arnao | 128/368 |
| 1,772,501 | 8/1930 | Shelton | 604/289 X |
| 1,917,712 | 7/1933 | Hamlet | 4/537 |
| 1,930,038 | 10/1933 | Crowley et al. | |
| 3,152,240 | 10/1964 | Scott | |
| 3,745,306 | 7/1973 | Naritomi | 34/97 X |
| 3,749,092 | 7/1973 | Williams | 128/256 |
| 3,947,659 | 3/1976 | Ono | 34/97 X |
| 4,292,971 | 10/1981 | Smit et al. | 128/256 |
| 4,300,556 | 11/1981 | Ochi et al. | 604/291 |
| 4,399,349 | 8/1983 | Deming et al. | 219/276 |
| 4,525,623 | 6/1985 | Da Silva | 34/96 X |
| 4,936,027 | 6/1990 | Tsuji | 34/97 X |

Primary Examiner—C. Fred Rosenbaum
Assistant Examiner—Corrine Maglione
Attorney, Agent, or Firm—Shlesinger, Arkwright & Garvey

[57] ABSTRACT

A steaming device includes a reservoir for containing a predetermined quantity of water, a heater for heating the water and producing the steam, a nozzle for exhausting out the steam, and a conduit for connecting the nozzle with the reservoir. The nozzle includes a pivotable flow adjusting mechanism for selectively varying the direction of steam flowing out therefrom.

16 Claims, 5 Drawing Sheets

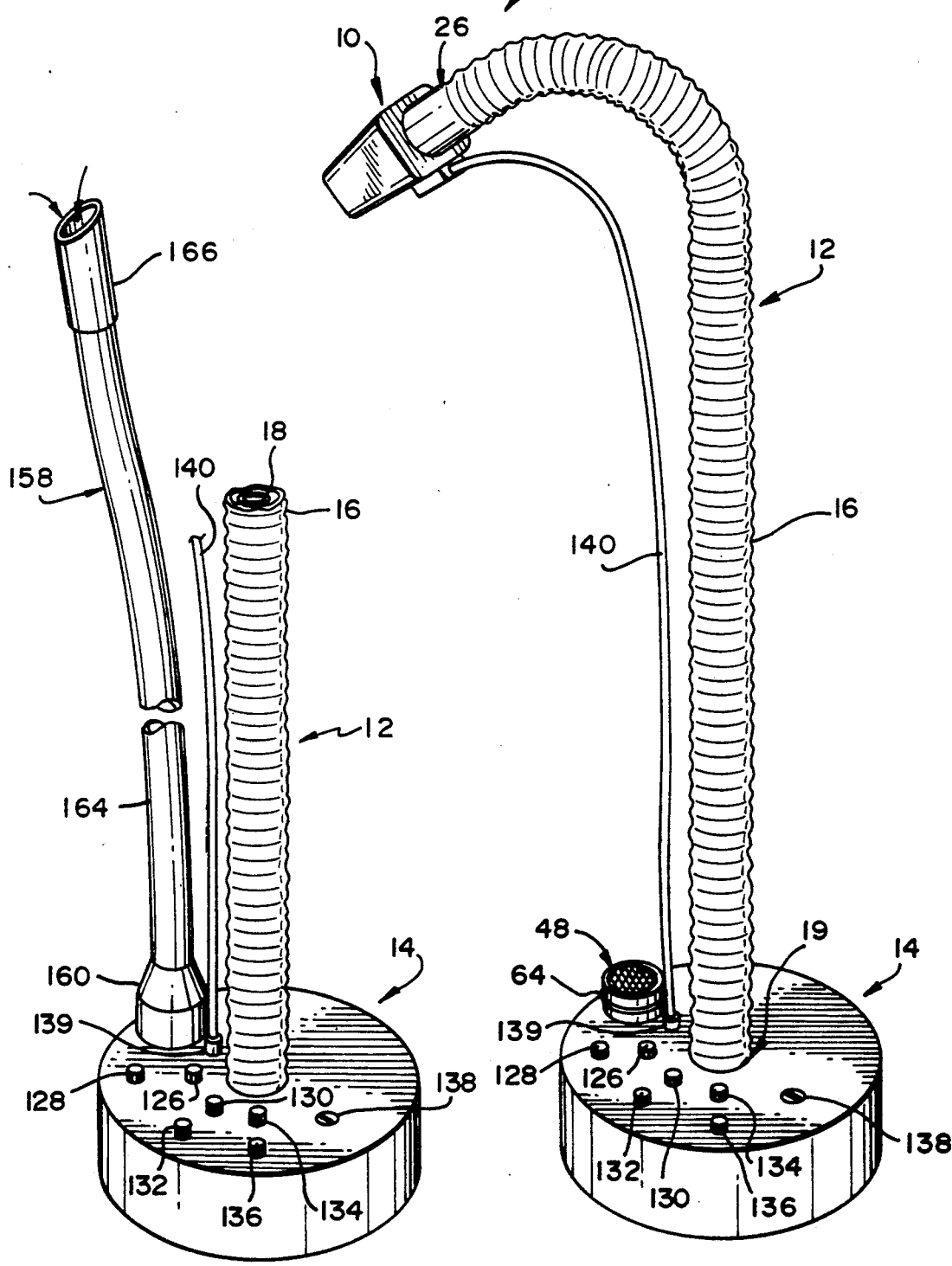

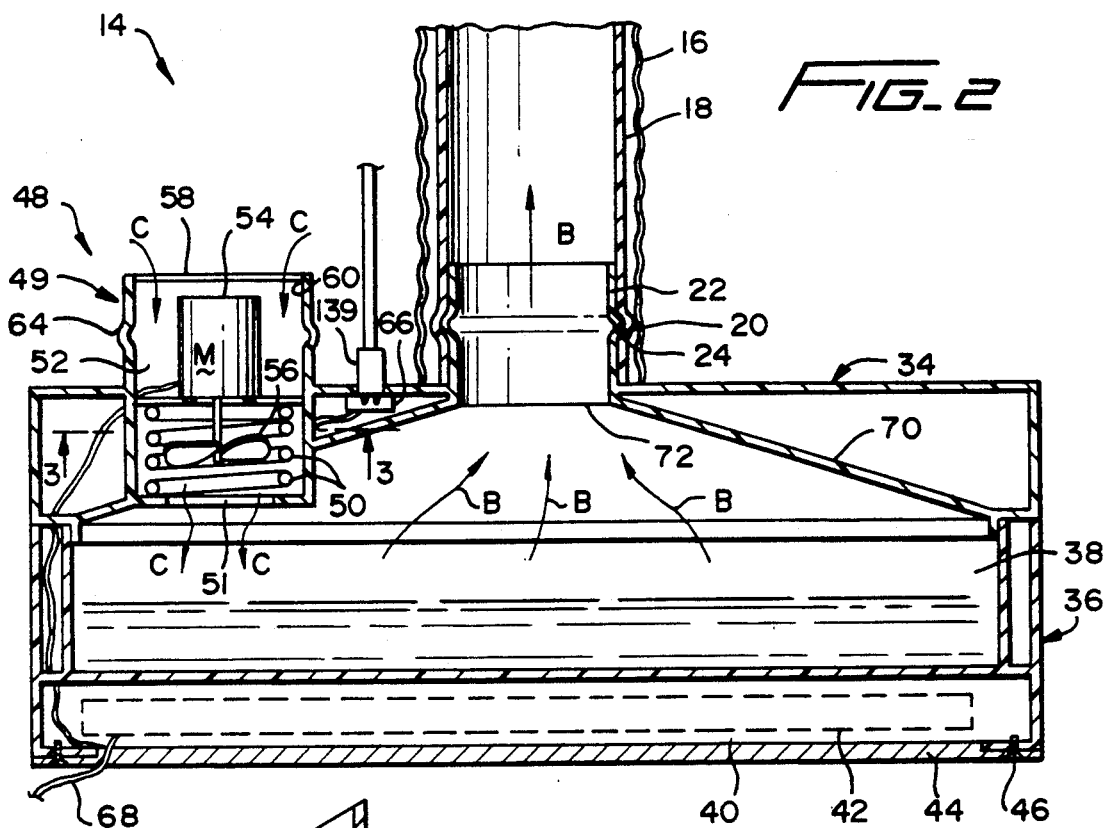

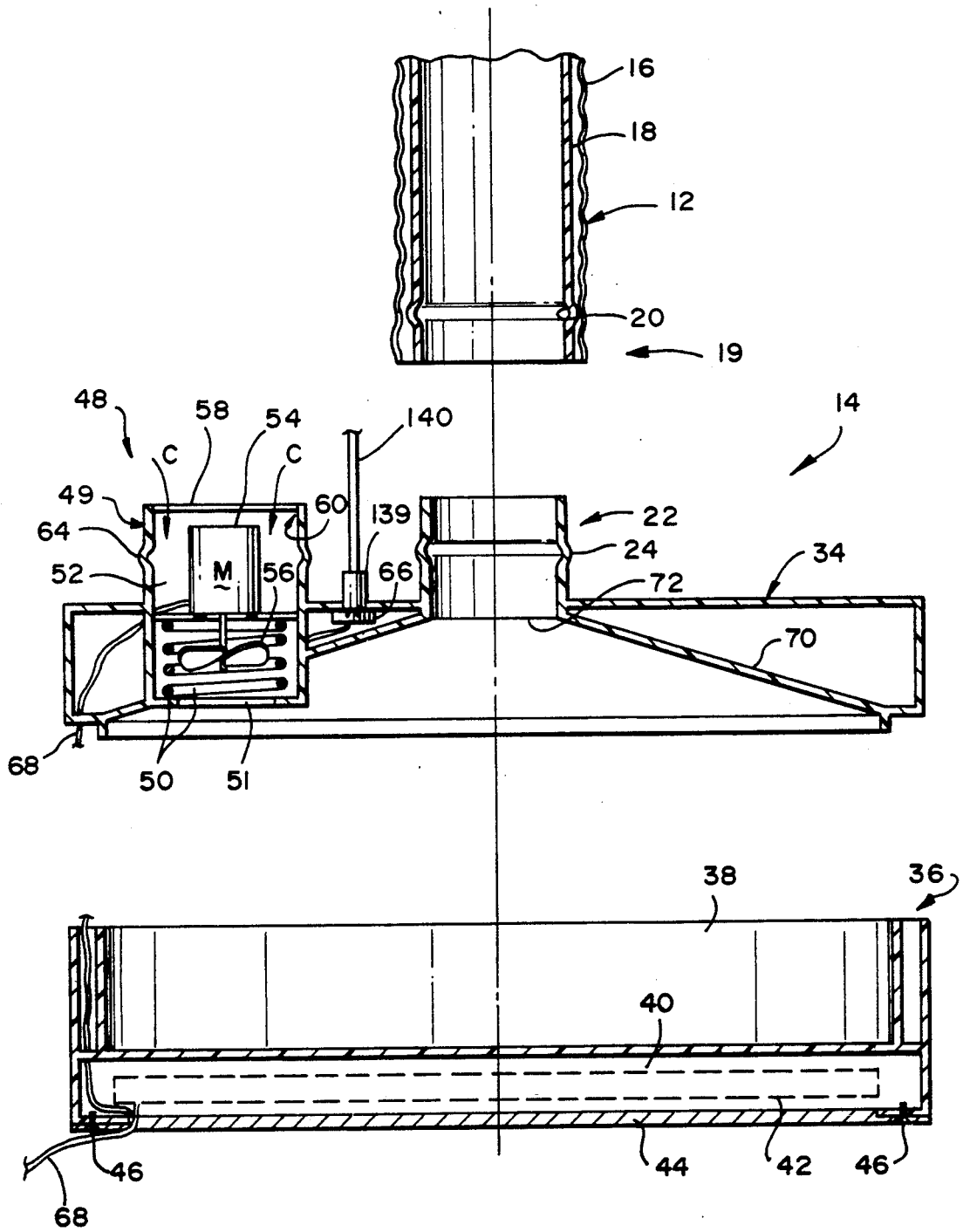
FIG_4

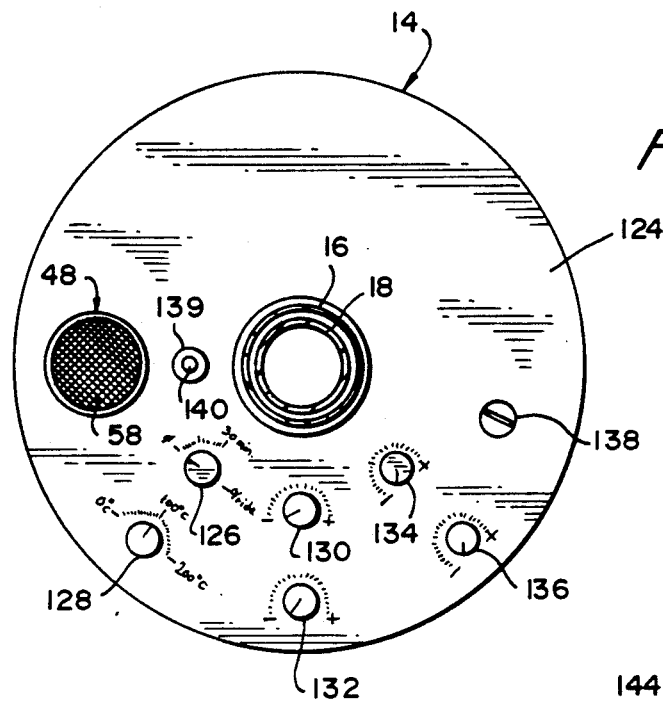
FIG_8
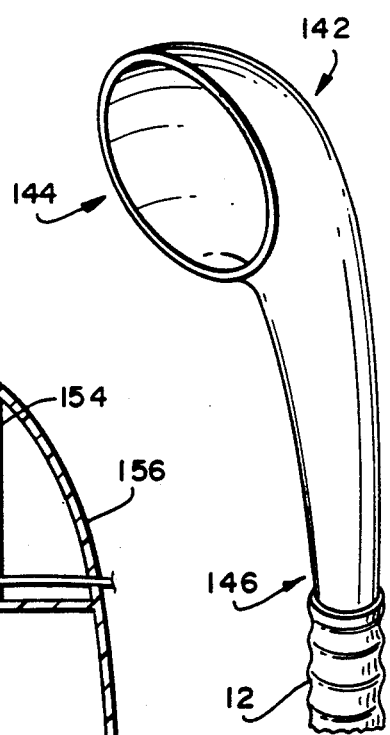
FIG_11
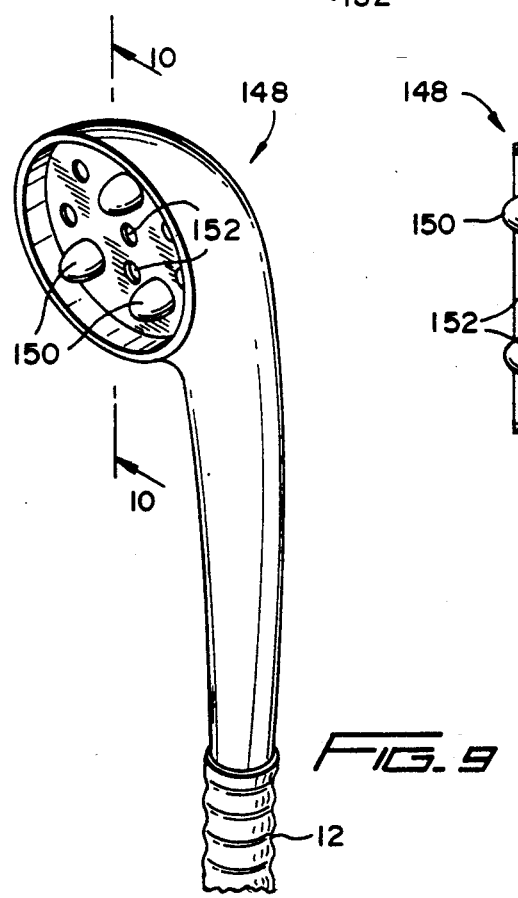
FIG_9
FIG_10

1

STEAMING DEVICE FOR COSMETIC SKIN TREATMENT

FIELD AND HISTORICAL BACKGROUND OF THE INVENTION

The present invention is directed to a steaming device, and more particularly to a cosmetic skin treatment device for applying heat in the form of steam to an area of human skin, as well as vacuuming the same for thereby cleaning it.

The human skin has been known to develop various disorders as a result of chemical imbalances in the body, adverse atmospheric conditions, etc. One of the main skin disorders that most persons suffer from, especially during their teenage years, is "acne". This disorder develops due to endocrine activity of certain glands in the body during the adolescence. Among others, this endocrine gland activity affects the sebaceous glands of the skin. Due to this activity, an oily substance, known as "sebum" tends to collect and clog pores in the skin thereby producing the acne disorder. The acne tends to blemish the skin which, from appearance, as well as the psychological point of view, is undesirable. One way to eliminate or substantially reduce the effects of acne, has been to periodically cleanse the skin by first applying heat to the skin for thereby opening the pores, and then removing the oily substance therefrom.

Various skin treatment devices have been proposed, and a few examples are shown in U.S. Pat. Nos. 1,421,756; 1,930,038; 3,152,240; 3,749,092; 4,292,971; and 4,399,349. The conventional devices, however, suffer from the disadvantage that they produce an intense flow of steam which is continuously directed to a specific portion of the skin. Due to this arrangement, the skin is prone to scalding or scorching. In addition, only a relatively small area of the skin can be subjected to steaming or heating at one time, due to the fact that in conventional systems the user has to manipulate the steam exhaust nozzle in order to heat or steam, for example, another area of the skin. Therefore, there is a need in the art for a steaming device which does not suffer from the disadvantages noted above.

OBJECTS AND SUMMARY OF THE INVENTION

The principal object of the present invention is to provide a steaming device for use in connection with steaming or heating human skin that does not suffer the disadvantages associated with conventional devices.

An object of the present invention is to provide a steaming device which can be used to steam or heat an area of human skin as well as to vacuum the skin for cleansing the same.

Another object of the present invention is to provide a steaming device which is simple in construction, easy to use and relatively inexpensive to manufacture.

Yet another object of the present invention is to provide a steaming device which is versatile in that it can be used to steam or heat a smaller skin area as well as to heat or steam a relatively large area of the skin.

An additional object of the present invention is to provide a steaming device which can be easily and quickly disassembled to a compact size for shipment purposes, and easily assembled in a relatively short time for use.

Still an additional object of the present invention is to provide a steaming device which can be easily converted from a floor supported device to a table top appliance, and vice-versa.

Still yet an additional object of the present invention is to provide a steaming device which can be easily converted to a steam massaging device.

A further object of the present invention is to provide a steaming device which is lightweight and portable.

Still a further object of the present invention is to provide a steaming device which can be used as a room humidifier.

Still yet a further object of the present invention is to provide a steaming device which can be used for light misting of household plants.

In summary, the main object of the present invention is to provide a steaming device which is versatile, easy to manufacture and safe to use.

BRIEF DESCRIPTION OF THE DRAWINGS

The above and other objects and advantages and novel features of the present invention will become apparent from the following detailed description of the preferred embodiment of the invention illustrated in the accompanied drawings, wherein:

FIG. 1 is a perspective elevational view of the steaming device of the present invention;

FIG. 2 is an enlarged partial longitudinal sectional view of the base section of the device shown in FIG. 1;

FIG. 3 is an enlarged sectional view taken along line 3—3 of FIG. 2;

FIG. 4 is a partial exploded view of the device shown in FIG. 2;

FIG. 8 is an enlarged top plan view of the base section shown in FIG. 1, with the neck in cross-section;

FIG. 9 illustrates an optional massaging attachment for the device;

FIG. 10 is a sectional view taken along line 10—10 of FIG. 9;

FIG. 11 illustrates another optional attachment for the device;

FIG. 12 is a partial perspective elevational view of the device shown in FIG. 1, with optional vacuum attachment; and FIG. 13 is an enlarged longitudinal sectional view of the vacuum attachment shown in FIG. 12.

DETAILED DESCRIPTION OF THE INVENTION

Figure 5:
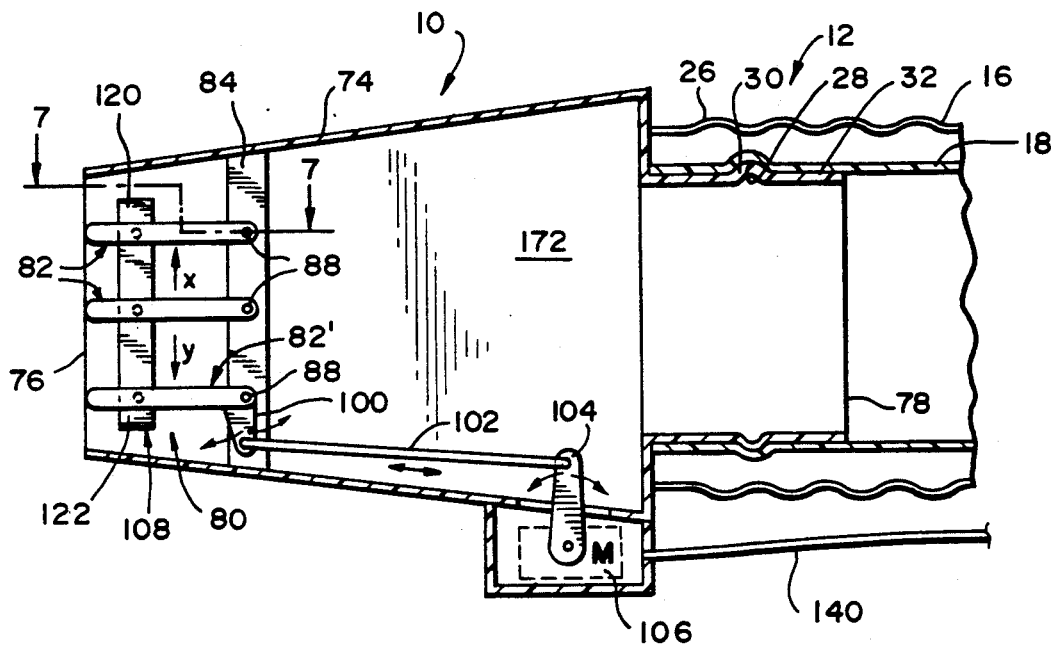
FIG. 5 is an enlarged partial longitudinal sectional view of the nozzle section of the device shown in FIG. 1.

As best shown in FIG. 1, the steaming device A of the present invention is comprised of nozzle section 10, neck section 12 and base section 14. The device A preferably has a total length of between six (6) to eight (8) feet and is constructed so as to be supported on the floor. It should be understood, however, that the steaming device A of the present invention can be constructed so as to be a table top model.

As best shown in FIGS. 2, 4 and 12, neck section 12 is tubular in configuration and includes an external upright, flexible and adjustable and substantially rigid support tube 16 that accommodates therein steam conduit 18 made of a rubber like or other suitable material.

As shown in FIG. 4, conduit 18 includes an annular groove 20 at its lower end 19 for snap-fitting neck section 12 over centrally positioned and upwardly extending tubular projection 22 of base section 14. The projection 22 includes an outwardly protruding annular rib 24 which is received in groove 20. The diameter of rib 24 is slightly greater than the diameter of groove 20 in order that neck section 12 is securely fitted over projection 22.

As shown in FIG. 5, the upper end 26 of neck section 12 also includes annular groove 28 for snugly receiving annular rib 30 provided in nozzle extension 32. The annular rib and groove arrangement so provided offers the ease of disconnecting neck section 12 from nozzle and base sections 10 and 14, for disassembly, maintenance, etc.

As best shown in FIGS. 2 and 4, base section 14 is comprised of interfitting upper and lower sections 34 and 36, respectively. When put together, upper and lower sections 34 and 36 define therein reservoir 38 for containing water which, when heated, is converted into steam, shown by arrows B in FIG. 2. The steam is flown through conduit 18 to be ultimately exhausted out through nozzle section 10. The lower section 36 includes chamber 40 for accommodating therein heating element 42. The chamber 40 is open at the bottom and a metal or lead base plate 44 is mounted therein by conventional screws 46, shown in FIG. 4. The base plate 44, when removed, provides easy access to chamber 40 for servicing heating element 42. In addition, base plate 44 is made of a relatively dense and heavier material and, therefore, adds to the vertical stability of the overall configuration of the steaming device A.

The upper section 34 includes condensation reduction system 48 for drawing atmospheric air into reservoir 38. The system 48 is generally comprised of housing 49 and includes rows of heating coils 50 coaxially positioned within passageway 52 leading to reservoir 38 via opening 51 (FIG. 3). A suction motor 54 for driving fan 56 is provided for drawing air from the exterior into passageway 52. A protective grill 58 is mounted in the top opening 60 of housing 49 for preventing various objects, contaminants, etc., from entering into system 48.

The air, entering into condensation reduction system 48, shown by arrows C, is heated by coils 50 to eliminate or reduce the degree of condensation when the air is mixed with the steam in reservoir 38. In FIG. 3, reference numeral 62 designates web plate 62 for supporting thereon the motor 54.

The housing 49 includes an outwardly protruding annular rib 64 for snap-fitting an attachment thereon, described below in more detail. A conventional electric outlet 66 is provided adjacent projection 22 for supplying power to nozzle section 10. An electric cable 68, to be connected to a power source (not shown), supplies power to heating element 42, motor 54 and outlet 66.

As shown in FIGS. 2 and 4, upper section, 34 includes a downwardly inclined annular ceiling member 70, extending from reservoir opening 72 to the periphery thereof, for directing and concentrating the flow of steam towards opening 72.

Figure 6:
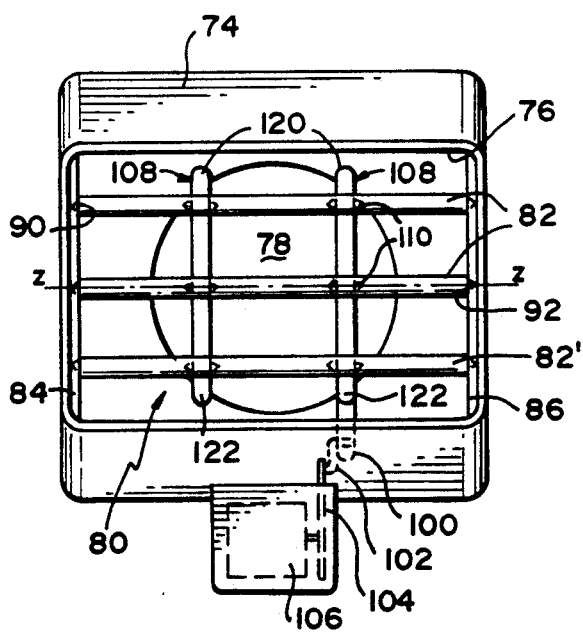
FIG. 6 is an enlarged front elevational view of the nozzle shown in FIG. 5.

As best shown in FIGS. 5 and 6, nozzle section 10 includes a converging nozzle 74 with opening 76 communicating with the exterior. Diametrically opposite opening 76 is nozzle opening 78 that communicates with steam conduit 18. As best shown in FIG. 6, nozzle 74 includes flow adjusting mechanism 80 mounted adjacent opening 76. The mechanism 80 includes horizontally oriented slats 82 pivotally mounted on side mounts 84 and 86 of nozzle 74.

Figure 7:
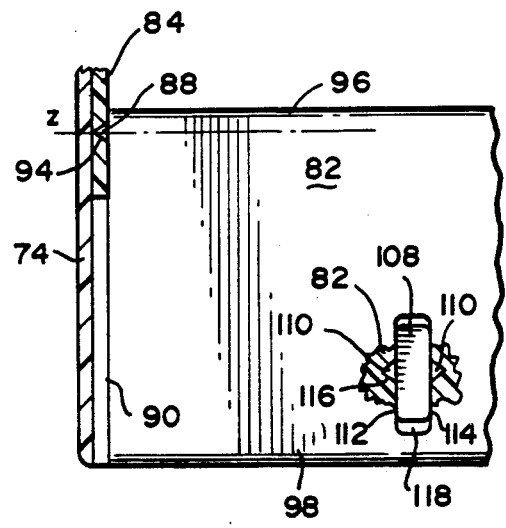
FIG. 7 is an enlarged sectional view taken along line 7—7 of FIG. 5.

Each horizontal slat 82 includes outwardly projecting triangular tabs 88 extending from the side edges 90 and 92 thereof. The tabs 88 are received into corresponding recesses 94 provided in sidewall mounts 84 and 86 (FIG. 7). In this manner, the front and rear ends 96 and 98 of each horizontal slat 82 remain free and the slats 82 pivot or deflect vertically about axis z from edges 90 to 92 and through tabs 88, as shown in FIG. 6. As best shown in FIG. 6, slats 82 are disposed horizontally in a vertically stacked, but spaced relationship to one another. The lowermost horizontal slat 82', however, as shown in FIG. 5, includes pivoting member 100, which is connected via shaft 102 to the oscillating member 104 connected to motor 106.

The mechanism 80 further includes two vertical slats 108, which are disposed in a side by side relationship and are interconnected with slats 82, shown in FIG. 6. Each vertical slat 108, as best shown in FIGS. 6 and 7, includes three pairs of triangular mounting tabs 110 that extend laterally from side surfaces 112 and 114 thereof. The tabs 110 are pivotally received in corresponding recesses 116 in corresponding slats 82. The vertical slats 108 therefore extend through openings 118 in horizontal slats 102 and are pivotally held and suspended in between horizontal slats 82 to form a grille-like, crisscross configuration. As best shown in FIGS. 5 and 6, the top and bottom ends 120 and 122 of vertical slats 108 extend beyond upper- and lowermost horizontal slats 82. As would be apparent to those of ordinary skill in the art that, when motor 106 oscillates member 104, the member 100 also oscillates and causes horizontal and vertical slats 82 and 108, respectively, to move or deflect in a vertical direction, as shown by arrows X and Y in FIG. 5.

As shown in FIG. 8, various controls are provided on top surface 124 of base section 14. For instance, reference numeral 126 designates a timer control for operating system A for a desired period and reference numeral 128 designates a control for regulating temperature of the heating element 42. Likewise, reference numerals 130 and 132 are provided to control the fan speed and coil temperature of condensation reduction system 48, respectively. The reference numerals 134 and 136 control the angle of deflection and the speed with which horizontal and vertical slats 82 and 108 move when motor 106 is actuated. Preferably, slats 82 deflect up to an angle of 30°. The reference numeral 138 designates a safety lock that requires a key (not shown) in order to turn on the steaming device A. This feature guards the device against accidental operation and/or mishandling by children and other people inexperienced in operating this type of device. In FIGS. 1, 2, 4 and 12 reference numeral 139 designates a conventional electric plug, and reference numeral 140 designates an electric cable that runs between nozzle section 10 and base section 14 for providing power to motor 106. While not shown, it may be desirable to use mechanical fasteners, such as clips, to keep cable 140 tied to neck section 12 in a conventional manner to prevent the same from dangling, etc.

FIGS. 9-13 disclose various optional attachments that can be used in connection with the steaming device A of the invention. In particular, FIG. 11 discloses a funnel-shaped attachment 142 having a relatively large opening 144 through which the steam exits. The end 146 lying opposite to opening 144 can be snap-fitted, either over end 26 of neck section 12 or projection 22 in base section 14. This attachment provides the flexibility of treating a relatively large area of skin due to its large opening 144.

FIGS. 9-10 disclose attachment 148 similar to funnel-shaped attachment 142, with the added feature of massaging fingers 150 interspersed between steam holes 152. The attachment 148 includes a motor 154 or the like device located in the hood section 156 thereof for causing the movement of fingers 150. The attachment 148 could also be snap-fitted over end 26 of neck section 12 or projection 22 of base section 14.

FIGS. 12 and 13 disclose a tubular, vacuum attachment 158 that may be snap-fitted over condensation reduction system 48. As shown in FIG. 13, the attachment 158 preferably includes body section 160 with an annular groove 162, flexible nozzle section 164, and top section 166. The nozzle 164 includes a cup-shaped tip portion 168 for accommodating therein filter 170. The attachment 158 can be easily snapped-on system 48, as rib 64 thereof is snugly received in groove 162. It should be noted that since condensation reduction system 48 functions as a suction device, when attachment 158 is mounted over it, the steaming device A can be used as a vacuum. Alternatively, attachment 158 can be mounted over projection 22 and attachments 142 and 148 can be mounted over nozzle section 164 for allowing the user to comfortably and easily manipulate flexible, but substantially non-rigid, nozzle section 164 to steam treat an area of the skin.

USE AND OPERATION

In order to use the steaming device A of the present invention, a user merely snaps on neck section 12 over projection 22 of base section 14. Depending upon the need, the user then snaps on nozzle section 10 or any one of attachments 142 or 148 on the end 26 of neck section 12. The device A is then electrically connected by cable 68 to a power source (not shown), unlocked by the user by opening lock 138, and desired selections of time, temperature, fan speed, coil temperature, angle and speed of the deflecting slats in the flow adjusting mechanism 80, etc., are made by actuating knobs 126, 128, 130, 132, 134 and 136. After a certain time has elapsed, the water in reservoir 38 begins to turn into steam, which is mixed with the ambient air drawn into reservoir 38 via condensation reduction system 48. The steam mixed hot air then flows upwardly through conduit 18 and enters nozzle chamber 172. It should be noted that due to the constant flow of ambient air drawn into reservoir 38, and continuous production of steam therein, a fluid pressure is developed in reservoir 38, which propels the steam mixed hot air upwardly through conduit 18. When the air stream reaches nozzle chamber 172, it is further concentrated due to the converging configuration of nozzle 74 and is exhausted out through nozzle opening 76 in a streamline flow.

As shown in FIG. 5, if flow adjusting mechanism 80 has not been actuated, the slats 82 and 108 will not move or deflect, and the stream would be blown straight out horizontally and would only affect the area of skin lying directing in front of it. However, if the user wishes to obtain a sweeping action of the stream, motor 106 can be easily actuated to cause a vertical, reciprocating motion of the horizontal and vertical slats 82 and 108, respectively. This unique arrangement offers the flexibility of treating a relatively larger skin area, and further substantially reduces the danger of burning or scalding an area of skin which is otherwise continuously affected by the incoming stream of hot air. In other words, since the stream sweeps an area of the skin, rather than continuously bombard the same area over and over, the danger of burning is substantially reduced.

Once the user is finished steam treating an area of the skin, it may be desirable to vacuum-off the moisture, oily substance, etc., from the same area of the skin. This can simply be done by mounting nozzle attachment 158 over condensation reduction system 48 and turning off steam production in reservoir 38. Due to the suction action of fan 56, the user can easily vacuum-off undesirable substances from the skin.

In addition to the skin treatment, the device of the present invention can also be used to mist household plants simply by the orientation of nozzle section 10 over the plants.

As can be seen from the above, the device of the present invention is versatile, simple to use, and can be easily assembled and disassembled for use or compact shipment.

While this invention has been described as having a preferred design, it is understood that it is capable of further modifications, uses, and/or adaptations of the invention following in general the principle of the invention and including such departures from the present disclosure as come with known or customary practice in the art to which the invention pertains, and as may be applied to the central features hereinbefore set forth and fall with the scope of the invention or the limits of the claims appended hereto.

What I claim is:

1. A cosmetic skin treatment device, comprising:
   a) reservoir means including first and second chambers;
   b) said first chamber being separated by said second chamber in a fluid-tight manner and provided for containing therein a predetermined quantity of water;
   c) heater means disposed within said second chamber for heating the water in said first chamber thereby producing steam;
   d) nozzle means for exhausting the steam to the exterior;
   e) conduit means connecting said nozzle means with said first chamber and flowing the steam therethrough;
   f) flow adjusting means pivotally mounted in said nozzle means for selectively varying the direction of steam flowing out therefrom;
   g) said nozzle means including an opening communicating with the exterior; and
   h) said flow adjusting means comprising a generally planar first slat pivotally mounted in said opening.
2. The device of claim 1, and including:
   a) means for introducing ambient air in said reservoir means for mixing with steam.
3. The device of claim 2, wherein:
   a) said ambient air introducing means comprises a suction motor and heating means for heating the ambient air.
4. The device of claim 3, and including:
   a) attachment means for releasably mounting in cooperative engagement with said ambient air introducing means for using the device as a vacuuming device.
5. The device of claim 4, wherein:

a) said attachment means includes filter means for collecting and preventing any contaminants from entering said reservoir means.

6. The device of claim 1, wherein:
a) said conduit means comprises a flexible tubing.

7. The device of claim 1, and including:
a) attachment means for substituting said nozzle;
b) said attachment means including a steam discharge opening; and
c) said attachment means including skin massaging means disposed adjacent said steam discharge opening.

8. The device of claim 1, wherein:
a) said first slat is mounted generally horizontally in said opening;
b) said nozzle means includes a generally central longitudinal axis extending along the length thereof; and
c) said first slat pivots with an angle of up to about 30 relative to said horizontal axis.

9. The device of claim 8, and including:
a) a second slat mounted generally vertically in said opening; and
b) said second slat is operably connected to said first slat so that when said first slat is pivoted said second slat also pivots.

10. The device of claim 8, and including:
a) means for pivoting said first slat.

11. The device of claim 1, wherein:
a) said nozzle means is pivotable relative to said conduit means.

12. A steaming device, comprising:
a) reservoir means for containing therein a predetermined quantity of water;
b) heater means in operative engagement with said reservoir means for heating the water and thereby producing steam;
c) nozzle means for exhausting out the steam;
d) conduit means for connecting said nozzle means with said reservoir means;
e) said nozzle means including pivotable flow adjusting means for selectively varying the direction of the steam flowing out therefrom;
f) said nozzle means including an opening communicating with the exterior;
g) said nozzle means including a generally central longitudinal axis extending along the length thereof;
h) said flow adjusting means comprising first and second sets of slats mounted in said opening;
i) said first set comprising a plurality of generally planar slats mounted generally horizontally in said opening;
j) said second set comprising a plurality of generally planar slats mounted generally vertically in said opening; and
k) said slats in said first and second sets being interconnected and pivot together as one integral unit when any one slat in said first set is pivoted.

13. The device of claim 12, and including:
a) means for selectively pivoting said slats of said first and second sets.

14. The device of claim 12, wherein:
a) at least one of said slats of said first set pivots with an angle of up to about 30 relative to said longitudinal axis.

15. The device of claim 12, wherein:
a) said horizontal slats are vertically spaced from one another and are disposed in a stacked relationship;
b) each of said horizontal slats includes first and second ends; and
c) each of said horizontal slats includes mounting means located adjacent said second end thereof;
d) whereby said horizontal slats pivot in said opening about corresponding mounting means.

16. The device of claim 15, wherein:
a) said vertical slats are suspended in said first set of horizontal slats.

* * * * *